(12) United States Patent
McKenzie-McHarg

(10) Patent No.: US 11,134,866 B2
(45) Date of Patent: Oct. 5, 2021

(54) GARMENTS, SYSTEMS AND METHODS FOR SPORTS TRAINING

(71) Applicant: 776BC INTERNATIONAL PTY LTD, South Melbourne (AU)

(72) Inventor: Cameron McKenzie-McHarg, South Melbourne (AU)

(73) Assignee: 776BC International Party Limited, South Melbourne (AU)

( * ) Notice: Subject to any disclaimer, the term of this patent is extended or adjusted under 35 U.S.C. 154(b) by 0 days.

(21) Appl. No.: 16/313,362

(22) PCT Filed: Jun. 30, 2017

(86) PCT No.: PCT/AU2017/050679
§ 371 (c)(1),
(2) Date: Dec. 26, 2018

(87) PCT Pub. No.: WO2018/000048
PCT Pub. Date: Jan. 4, 2018

(65) Prior Publication Data
US 2019/0150531 A1 May 23, 2019

(30) Foreign Application Priority Data

Jun. 30, 2016 (AU) ............................... 2016902573
Mar. 27, 2017 (AU) ............................... 2017901083

(51) Int. Cl.
*A61B 5/11* (2006.01)
*A41D 31/18* (2019.01)
(Continued)

(52) U.S. Cl.
CPC ........ *A61B 5/1127* (2013.01); *A41D 13/0015* (2013.01); *A41D 31/18* (2019.02); *A61B 5/11* (2013.01)

(58) Field of Classification Search
CPC .......... G06K 9/00342; G06K 9/00724; G06K 9/00751; G06K 9/78; G06K 9/00362;
(Continued)

(56) References Cited

U.S. PATENT DOCUMENTS 3,381,307 A * 5/1968 Shingler ................. A41D 13/01
2/94
3,683,419 A * 8/1972 Lewis ..................... A41D 27/08
2/67

(Continued)

OTHER PUBLICATIONS

International Search Report for International Patent Application No. PCT/AU2017/050679, dated Aug. 29, 2017.
(Continued)

*Primary Examiner* — Robert H Muromoto, Jr.

(57) ABSTRACT

A garment including: fabric configured to conform to a body portion of a wearer; at least one front-transverse segmental marker visible on a front exterior surface of the garment in use and extending parallel to a transverse axis of the body portion; at least one rear-transverse segmental marker visible on a rear exterior surface of the garment in use and extending parallel to the transverse axis of the body portion; at least one front-longitudinal segmental marker visible on a front exterior surface of the garment in use and extending parallel to a longitudinal axis of the body portion; at least one rear-longitudinal segmental marker visible on a rear exterior surface of the garment in use and extending parallel to the longitudinal axis of the body portion; and at least one side-longitudinal segmental marker visible on each side exterior surface of the garment in use and extending parallel to the longitudinal axis of the body portion.

4 Claims, 16 Drawing Sheets

(51) Int. Cl.
*A41D 13/00* (2006.01)
*A61B 5/103* (2006.01)

(58) Field of Classification Search
CPC .............. G06K 9/6231; G09B 19/0038; G09B 19/003; A61B 2503/10; A61B 2505/09; A61B 5/0024; A61B 5/1126; A61B 5/6804; A61B 5/11; A61B 2562/0247; A61B 2562/046; A61B 5/002; A61B 5/1071; A61B 5/1121; A61B 5/6831; A61B 5/1124; A61B 5/00; A61B 5/1114; A61B 5/1128; A61B 5/486; A61B 5/6895; A61B 5/7264; A41D 13/0015; A41D 13/01; A41D 13/1281; A41D 13/02; A41D 1/002; A41D 2600/10; A41D 31/04; G06F 19/3481; G06F 3/011; G06F 3/017; G06F 19/00; G06F 1/163; G06F 3/014; G06F 19/36; G06F 19/34; G06F 3/0304; A63B 71/0622; A63B 2071/0655; A63B 2071/0661; A63B 2071/0694; A63B 2220/833; A63B 2225/20; A63B 2225/50; A63B 2220/05; A63B 2220/12; A63B 2220/18; A63B 2220/40; A63B 2220/803; A63B 2220/836; A63B 24/00; A63B 24/0003; A63B 24/0006; A63B 24/0021; A63B 24/0062; A63B 69/00; A63B 71/141; G06T 2207/30221; G06T 2207/30196; G06T 7/20; G06T 2207/10016; G06T 2207/30241

See application file for complete search history.

(56) References Cited

U.S. PATENT DOCUMENTS

| | | | | |
|---|---|---|---|---|
| 3,790,963 | A * | 2/1974 | Ealy | A41D 13/02 2/79 |
| 4,365,354 | A * | 12/1982 | Sullivan | A41D 13/01 2/171 |
| 4,815,146 | A * | 3/1989 | Theewis | A41D 13/01 2/94 |
| 5,588,156 | A * | 12/1996 | Panton, Jr. | A41D 13/01 2/115 |
| 5,819,322 | A * | 10/1998 | Dicker | A41D 13/0015 2/456 |
| 5,836,016 | A * | 11/1998 | Jacobs | A41D 7/00 2/69 |
| 5,946,721 | A * | 9/1999 | Dance | A41D 13/01 2/69 |
| 6,591,590 | B1 * | 7/2003 | Henneberg | A41D 19/01552 473/205 |
| 7,500,274 | B1 * | 3/2009 | Kallen | A41D 1/086 2/227 |
| 8,428,357 | B2 * | 4/2013 | Stephenson | A63B 24/0003 348/135 |
| 8,707,463 | B2 * | 4/2014 | Orloff | A41D 13/0015 2/22 |
| 8,863,316 | B2 * | 10/2014 | Gaskins | A41D 19/01547 2/161.1 |
| 9,241,516 | B2 * | 1/2016 | Sokolowski | A41D 13/0015 |
| 9,582,072 | B2 * | 2/2017 | Connor | G06F 3/011 |
| 9,589,207 | B2 * | 3/2017 | Holohan | G06F 19/3481 |
| 9,619,891 | B2 * | 4/2017 | Bose | G06K 9/00342 |
| 9,886,559 | B1 * | 2/2018 | McNair | G06F 19/36 |
| 9,936,891 | B2 * | 4/2018 | Marcarian | A61B 5/0488 |
| 9,999,805 | B2 * | 6/2018 | Ahuja | A63B 24/0062 |
| 10,021,430 | B1 * | 7/2018 | Lewis | H04N 21/231 |
| 10,039,332 | B2 * | 8/2018 | Sokolowski | A63B 71/0622 |
| 10,095,952 | B2 * | 10/2018 | Zhao | G06K 9/4638 |
| 10,096,118 | B2 * | 10/2018 | Huang | G06K 9/4642 |
| 10,109,061 | B2 * | 10/2018 | Bose | A63F 13/211 |
| 10,124,230 | B2 * | 11/2018 | Thornbrue | G01C 21/00 |
| 10,180,721 | B2 * | 1/2019 | Hoen | G06F 3/014 |
| 10,212,986 | B2 * | 2/2019 | DePietro | G16H 20/30 |
| 10,234,934 | B2 * | 3/2019 | Connor | A41D 13/1281 |
| 10,265,602 | B2 * | 4/2019 | Haas | A63B 71/0619 |
| 10,269,169 | B2 * | 4/2019 | Sullivan | G03B 35/00 |
| 10,321,873 | B2 * | 6/2019 | Connor | A61B 5/1126 |
| 10,406,399 | B2 * | 9/2019 | Bentley | A63F 13/332 |
| 10,602,965 | B2 * | 3/2020 | Connor | A61B 5/6804 |
| 10,664,690 | B2 * | 5/2020 | Holohan | G16H 20/30 |
| 2002/0183961 | A1 * | 12/2002 | French | A63B 24/0003 73/379.04 |
| 2003/0150043 | A1 * | 8/2003 | Koppes | A41D 31/32 2/69 |
| 2003/0196251 | A1 * | 10/2003 | Lee | A42B 1/242 2/244 |
| 2004/0143882 | A1 * | 7/2004 | Gardner | A41D 13/01 2/81 |
| 2004/0158911 | A1 * | 8/2004 | Amnuel | A41B 9/06 2/115 |
| 2005/0037844 | A1 * | 2/2005 | Shum | A63F 13/06 463/36 |
| 2005/0265580 | A1 * | 12/2005 | Antonucci | G06K 9/00342 382/103 |
| 2005/0268371 | A1 * | 12/2005 | Meekins | A41D 27/08 2/69 |
| 2007/0000007 | A1 * | 1/2007 | MacDonald | A41D 13/0015 2/69 |
| 2007/0016999 | A1 * | 1/2007 | Harber | A41D 27/08 2/69 |
| 2007/0281812 | A1 * | 12/2007 | Smith | A63B 43/008 473/604 |
| 2007/0285744 | A1 * | 12/2007 | Boyer | G01J 3/462 358/518 |
| 2010/0137064 | A1 * | 6/2010 | Shum | A63F 13/06 463/36 |
| 2011/0007275 | A1 * | 1/2011 | Yoo | A61B 5/1127 351/209 |
| 2011/0052005 | A1 * | 3/2011 | Selner | G06K 9/00342 382/103 |
| 2014/0342844 | A1 * | 11/2014 | Mooney | A63B 24/0006 473/266 |

OTHER PUBLICATIONS

Written Opinion for International Patent Application No. PCT/AU2017/050679, dated Aug. 29, 2017.
International Preliminary Report on Patentability for International Patent Application No. PCT/AU2017/050679, dated Oct. 24, 2018.
Response to Written Opinion for International Patent Application No. PCT/AU2017/050679.

* cited by examiner

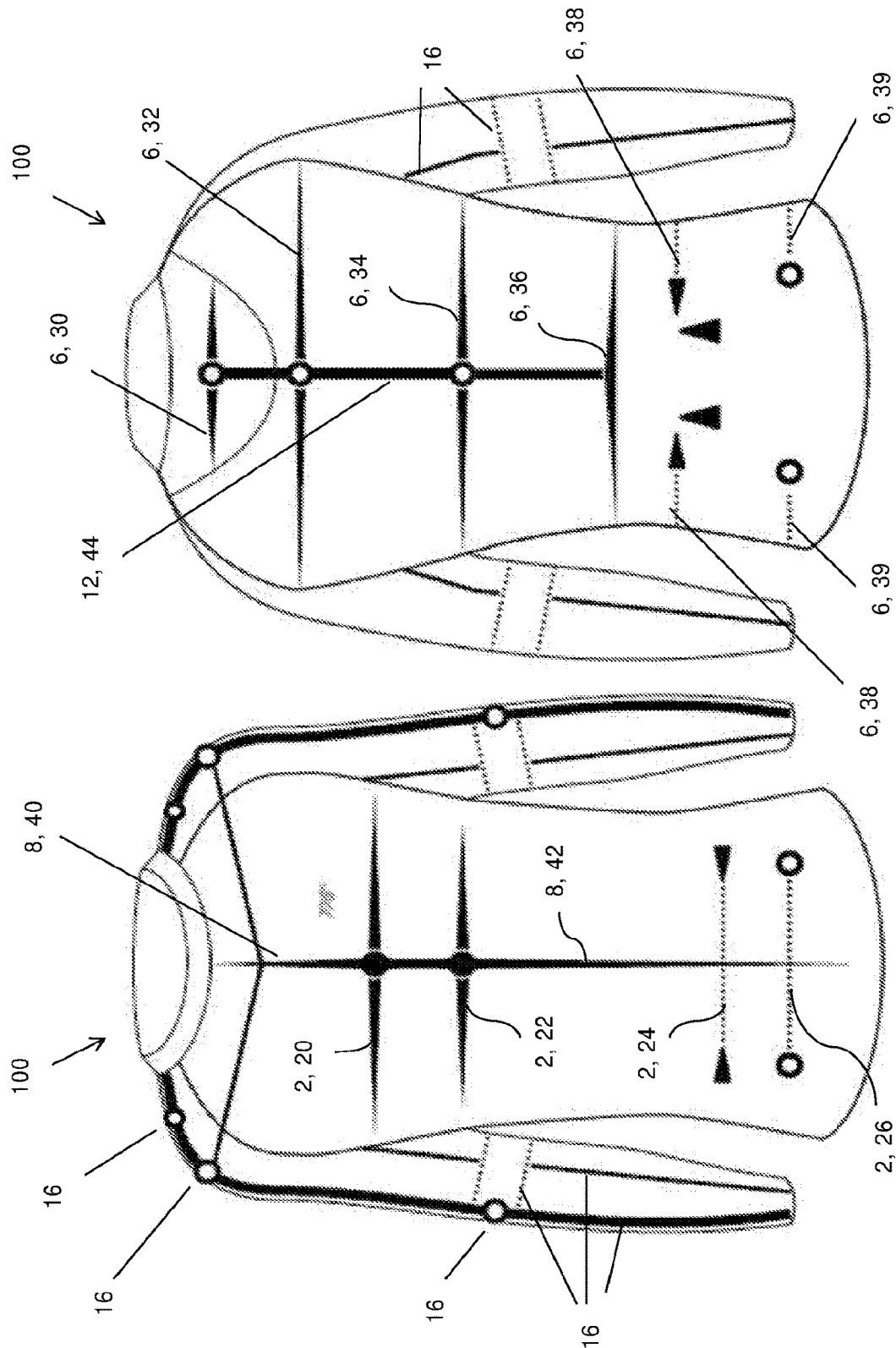

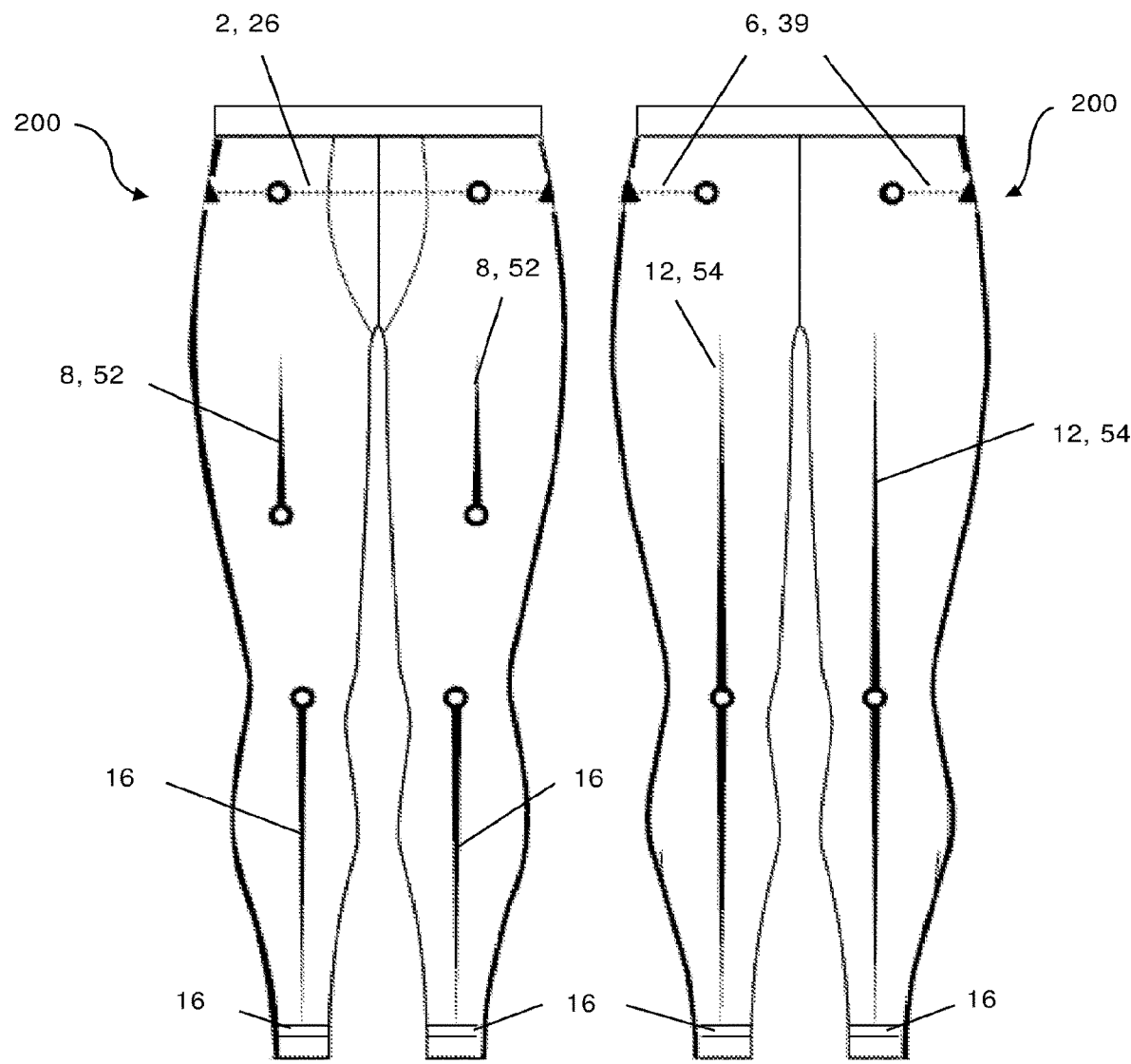

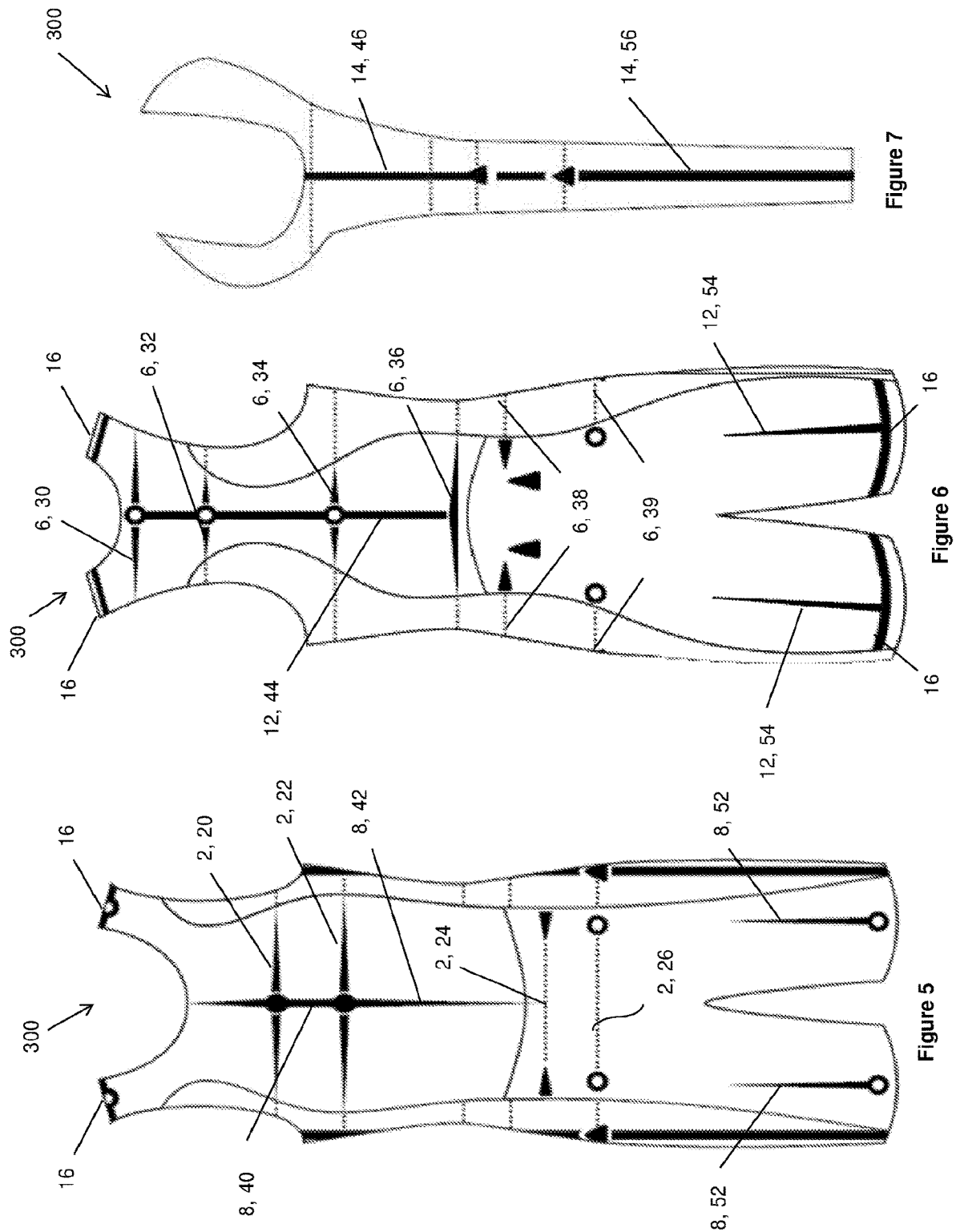

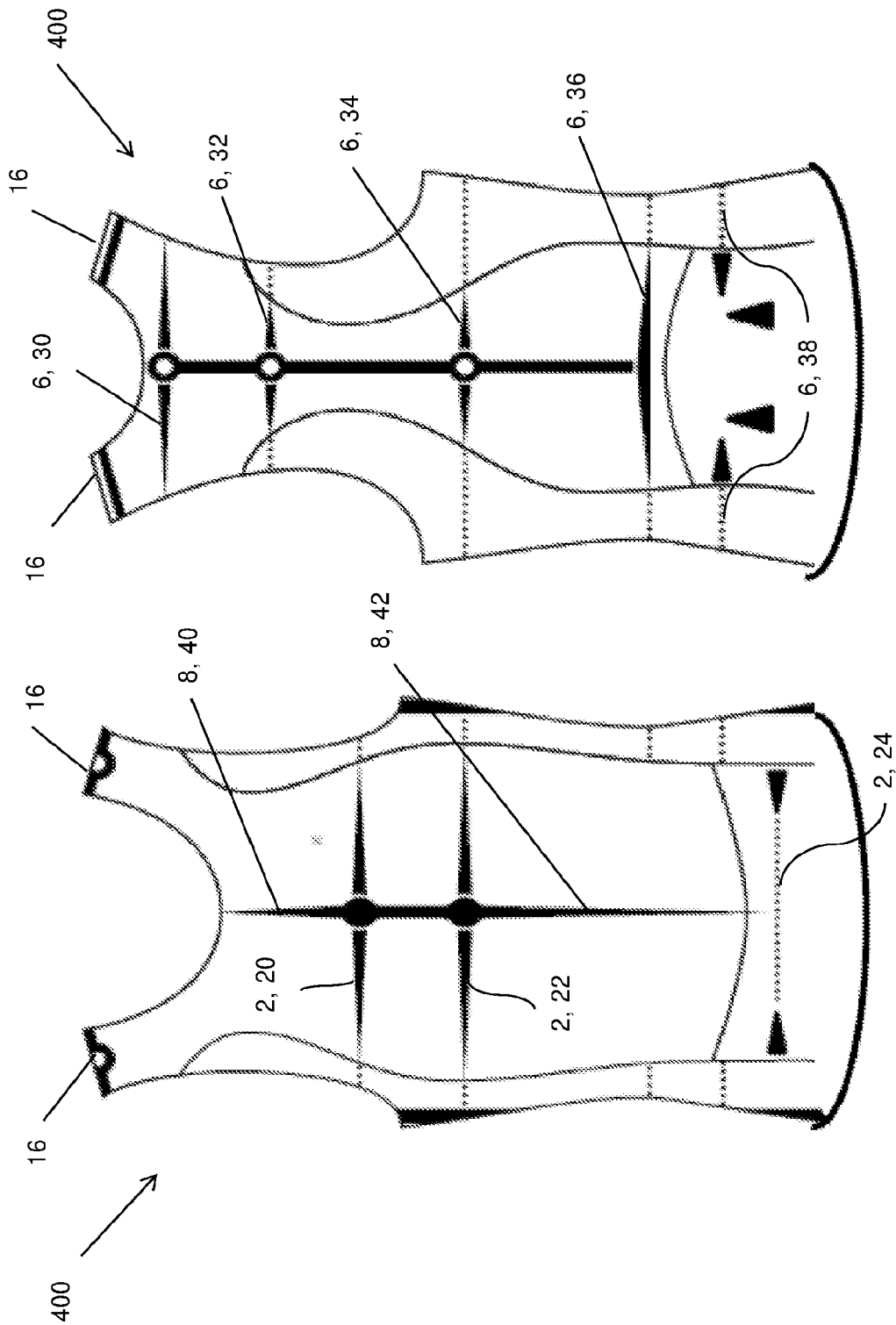

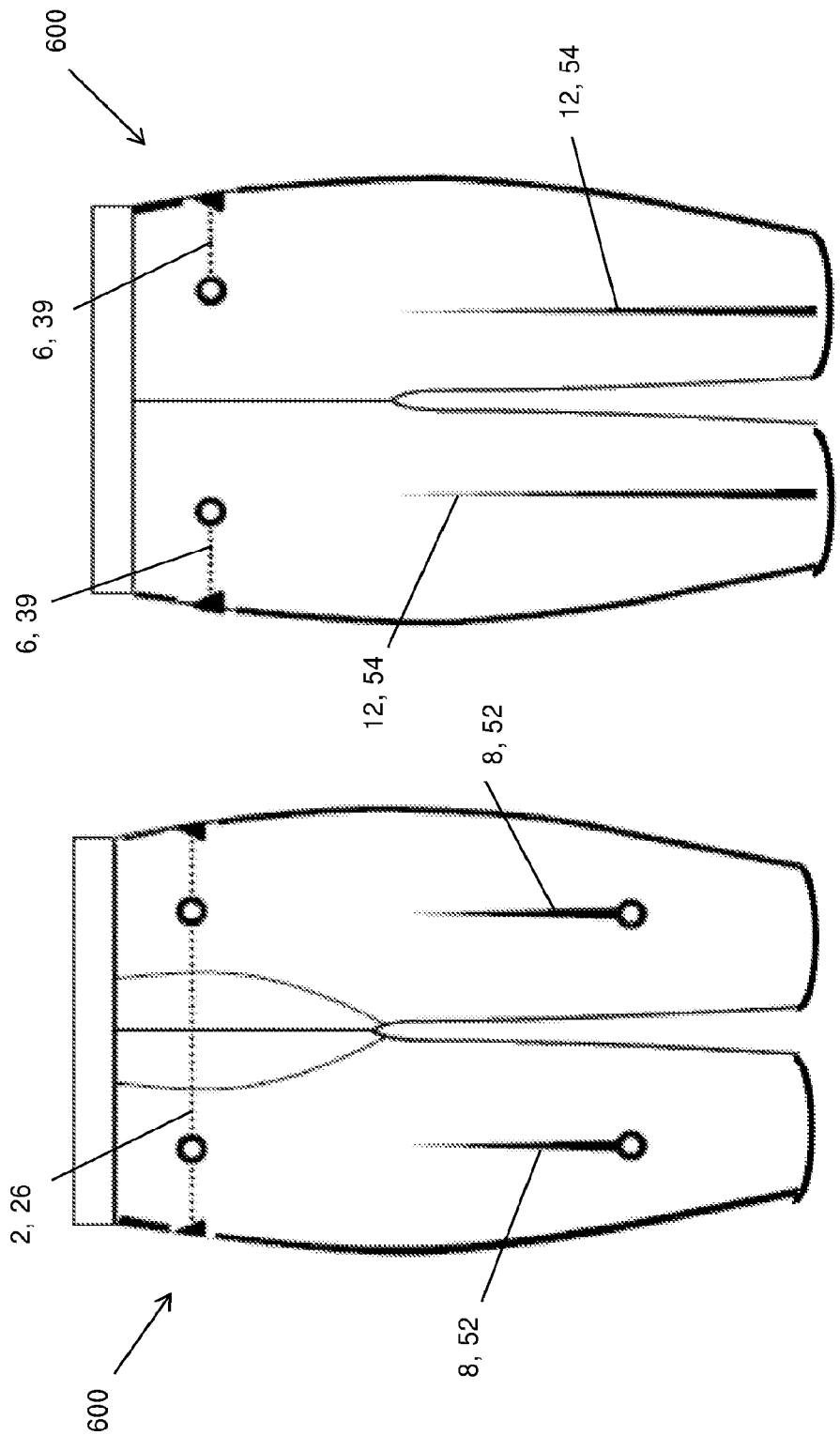

GARMENTS, SYSTEMS AND METHODS FOR SPORTS TRAINING

RELATED APPLICATIONS

This application is a 371 National Stage of International Patent Application No. PCT/AU/2017/050679, entitled "GARMENTS, SYSTEMS AND METHODS FOR SPORTS TRAINING" filed on Jun. 30, 2017, which claims priority to Australian Patent Application No. 2016902573, entitled "A GARMENT FOR WEARING ON A USER'S BODY," filed on Jun. 30, 2016 and Australian Patent Application No. 2017901083, entitled "GARMENTS, SYSTEMS AND METHODS FOR SPORTS TRAINING," filed on Mar. 27, 2017, both of which are herein incorporated by reference in their entireties.

FIELD

The present invention relates to garments, systems and methods for sports training and physical education.

BACKGROUND

Biomechanical analysis using optical motion tracking conventionally involves painstaking positioning of markers onto test subjects according to one of many marker placement protocols. Each test subject is then video-recorded under artificial, highly-controlled conditions, and the videos subsequently analysed to obtain positional data for kinematics and performance analysis.

These conventional systems are configured for analysing individual subjects performing isolated movements, and typically struggle with high speed or dynamic motion capture. These systems are also not designed for intersubject analysis and cannot provide insight into coordination and synergy between team mates.

Improved systems for biomechanical analysis have been proposed using garments with embedded sensors. The sensed data may be processed on a user device to provide feedback to the user. However, such systems rely on complex programming and complex underlying models of body movement and are therefore typically limited to only very specific movements. Such expensive systems are generally inaccessible by amateur athletes and the average gym-goer. Such systems typically also require specialist knowledge for interpreting the sensed data, and may overload the average user with too much data. Like conventional optical tracking, these sensor systems are also not designed for intersubject analysis.

In this context, there is a need for improved apparatus, systems and methods for sports training and physical education to address some of the issues above.

This application claims priority to Australian Provisional Applications Nos. 2016902573 and 2017901083, respectively filed on 30 Jun. 2016 and 27 Mar. 2017, which are incorporated by reference herein in their entirety.

SUMMARY

According to the present invention, there is provided a garment comprising:

fabric configured to conform to a body portion of a wearer;

at least one front-transverse segmental marker visible on a front exterior surface of the garment in use and extending parallel to a transverse axis of the body portion;

at least one rear-transverse segmental marker visible on a rear exterior surface of the garment in use and extending parallel to the transverse axis of the body portion;

at least one front-longitudinal segmental marker visible on a front exterior surface of the garment in use and extending parallel to a longitudinal axis of the body portion;

at least one rear-longitudinal segmental marker visible on a rear exterior surface of the garment in use and extending parallel to the longitudinal axis of the body portion; and at least one side-longitudinal segmental marker visible on each side exterior surface of the garment in use and extending parallel to the longitudinal axis of the body portion.

The garment may further comprise at least one peripheral marker visible on an exterior surface of the garment in use and positioned non-collinear with at least one of the segmental markers.

The body portion may be the wearer's torso. The front-transverse segmental marker may comprise one or more marks extending across a xiphisternal axis, lower ribs, pelvic crests or greater trochanters. The rear-transverse segmental marker may comprise one or more marks extending across an upper thoracic segment, a middle thoracic segment, a lower thoracic segment, a lumbar segment, pelvic crests or sacrum. The front-longitudinal segmental marker may comprise one or more marks extending along a midsternal line, linea alba, or a combination thereof. The rear-longitudinal segmental marker may comprise one or more marks extending along a vertebral line. The side-longitudinal segmental marker may comprise one or more marks extending along a midaxillary line, an anterior axillary line, or a posterior axillary line.

The body portion may be a portion of the wearer's lower body. The front-transverse segmental marker may comprise one or more marks extending across pelvic crests or greater trochanters. The rear-transverse segmental marker may comprise one or more marks extending across pelvic crests or sacrum. The front-longitudinal segmental marker may comprise one or more marks extending between an anterior superior iliac crest and a middle of a thigh. The rear-longitudinal segmental marker may comprise one or more marks extending between a a posterior superior iliac crest and a midpoint of a popliteal crease. The side-longitudinal segmental marker may comprise one or more marks extending between a greater trochanter and a lateral femoral epicondyle.

The garment may cover the wearer's torso and a portion of the wearer's lower body.

The segmental markers may be configured for multi-sport use, including rowing, cycling, paddling, swimming, athletics, weight lifting, running, walking, yoga, pilates, basketball, golf, football, tennis, baseball, gymnastics, dance, or aerobics.

The present invention also provides a system for training for and/or coaching of team sports, the system comprising a plurality of the garments as described to be worn by two or more players of the team, wherein the segmental markers provide visual feedback and comparison of movement among the players.

The present invention also provides a method for training for and/or coaching of a physical activity, the method comprising visually tracking movement of a wearer of the garment as described by observing one or more of: a) displacement and/or rotation of a peripheral marker or other body portion relative to a segmental marker, b) rotation of a segmental marker relative to another segmental marker, c) displacement and/or rotation of a segmental marker relative to an external reference.

The method may comprise visually tracking and comparing movement among multiple team players each wearing the garment as described.

The present invention also provides a system for training for and/or coaching of a physical activity, the system comprising:

an image capture device for capturing a visual recording of a wearer wearing a garment as described while performing one or more movements;

memory for storing a) the visual recording of the wearer and b) reference instructions comprising a visual recording of a demonstrator wearing a garment as described while performing the one or more movements;

a display device for displaying one or more of: a) the visual recording of the wearer, b) the reference instructions, and c) a visual comparison of the visual recording of the wearer and the reference instructions.

The system may further comprise a processor programmed to automatically identify one or more markers on the garment captured in one or more of a) the visual recording of the wearer, b) the reference instructions, and c) a visual comparison of the visual recording of the wearer and the reference instructions.

The system may further comprise a processor programmed to automatically measure or calculate one or more variables comprising angle between recorded markers, range of movement, sequence of movement, acceleration, and deceleration.

One or more of the image capture device, memory, display device and processor may be provided by a portable electronic device.

BRIEF DESCRIPTION OF DRAWINGS

Embodiments of the invention will now be described by way of example only with reference to the accompanying drawings, in which:

FIG. 1 is a front view of a garment according to one embodiment of the invention;

FIG. 2 is a rear view of the garment of FIG. 1;

FIG. 3 is a front view of a garment according to a second embodiment of the invention;

FIG. 4 is a rear view of the garment of FIG. 3;

FIG. 5 is a front view of a garment according to a third embodiment of the invention;

FIG. 6 is a rear view of the garment of FIG. 5;

FIG. 7 is a partial side view of the garment of FIG. 5;

FIG. 11 is a front view of a garment according to a fourth embodiment of the invention;

FIG. 12 is a rear view of the garment of FIG. 11;

FIG. 15 is a front view of a garment according to a sixth embodiment of the invention;

FIG. 16 is a rear view of the garment of FIG. 15;

DESCRIPTION OF EMBODIMENTS

Figures 13, 14:
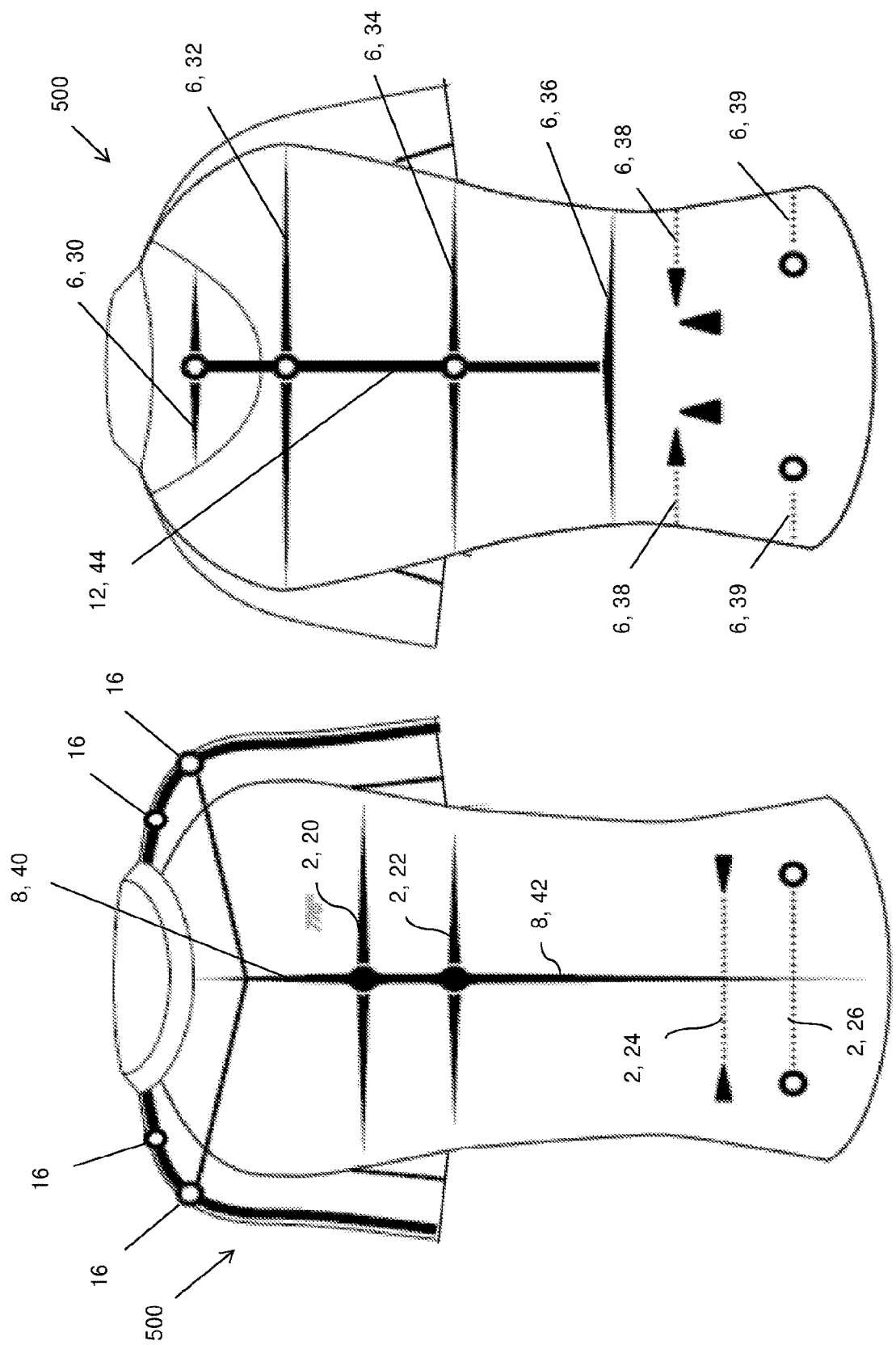
FIG. 13 is a front view of a garment according to a fifth embodiment of the invention.
FIG. 14 is a rear view of the garment of FIG. 13.

FIGS. 1 to 7 illustrate various embodiments of a garment for sports training and physical education. The garment comprises fabric configured to conform to a body portion of a wearer. Specifically, FIGS. 1 and 2 illustrate a long-sleeved top 100 configured to conform to a wearer's torso, FIGS. 3 and 4 illustrate a pair of tights 200 configured to conform to a wearer's lower body, FIGS. 5 to 7 illustrate a body suit 300 configured to conform to a wearer's upper body and a portion of the wearer's lower body, FIGS. 11 and 12 illustrate a singlet 400 configured to conform to a wearer's torso, FIGS. 13 and 14 illustrate a short-sleeved top 500 configured to conform to a wearer's torso, and FIGS. 15 and 16 illustrate a pair of shorts 600 configured to conform to a wearer's lower body.

Each of the garments 100, 200, 300, 400, 500, 600 comprises at least one front-transverse segmental marker 2 visible on a front exterior surface of the garment in use and extending parallel to a transverse axis 4 of the body portion. Each garment further comprises at least one rear-transverse segmental marker 6 visible on a rear exterior surface of the garment in use and extending parallel to the transverse axis 4 of the body portion. Each garment further comprises at least one front-longitudinal segmental marker 8 visible on a front exterior surface of the garment in use and extending parallel to a longitudinal axis 10 of the body portion. Each garment further comprises at least one rear-longitudinal segmental marker 12 visible on a rear exterior surface of the garment in use and extending parallel to the longitudinal axis 10 of the body portion. As illustrated most clearly in FIG. 7, each garment further comprises at least one side-longitudinal segmental marker 14 visible on each side exterior surface of the garment in use and extending parallel to the longitudinal axis 10 of the body portion. Each of the segmental markers 2, 6, 8, 12, 14 is located, at least in part, on the wearer's trunk in use.

These segmental markers 2, 6, 8, 12, 14 are lines which provide visual indicators of key segments of the human body. These segments are related to joint centres, bony landmarks and key functional pivot points and can be traced through specific lines (eg line of the spine) and points on the trunk. Because all human body movement occur around one or more of these key segments, the segmental markers 2, 6, 8, 12, 14 are key to assessing any form of movement in any of the body planes (ie the frontal, sagittal and transverse planes). That is, the specific selection of these segmental markers 2, 6, 8, 12, 14 is universally applicable to biomechanical analysis of any sport or physical activity. It has also been found that this specific selection of segmental markers 2, 6, 8, 12, 14 when placed on a garment according to the present invention optimises visual tracking of movement, ie provides sufficient information while reducing visual information overload.

For example, the segmental markers 2, 6, 8, 12, 14 provide visual indication of linear motion by the displacement of a segmental marker relative to an external reference, eg the ground, the horizon, or a vertical edge of a wall. This may be used to monitor movement of a weight-lifter's shoulders before he performs a deadlift, to track the height of a jump, etc.

Figure 10:
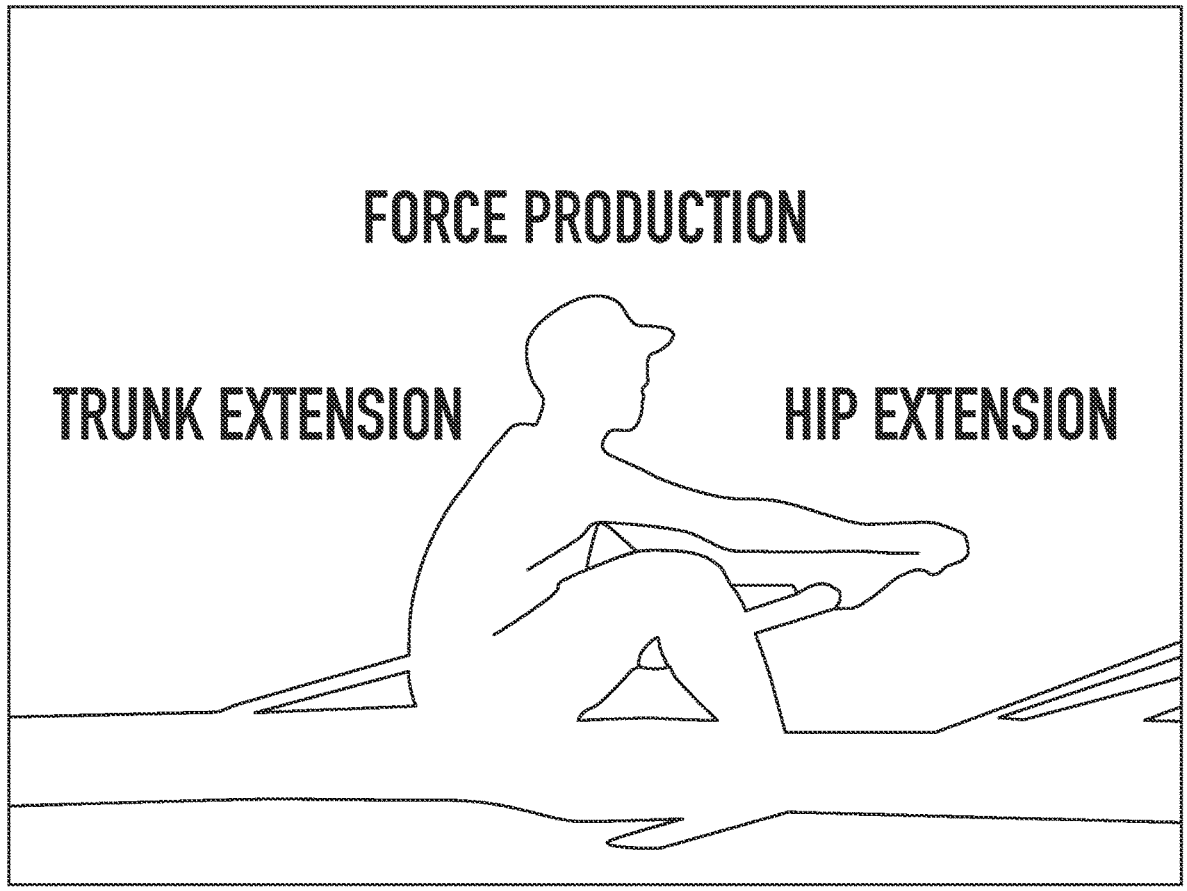
FIG. 10 is a side view of a rower, schematically illustrating a method of sports training according to one embodiment of the invention.

The segmental markers 2, 6, 8, 12, 14 may also provide visual indication of ranges of motion, since all rotation occur around the key segments. Specifically, the rotation of a segmental marker 2, 6, 8, 12, 14 relative to another segmental marker 2, 6, 8, 12, 14 can be used to monitor joint angles, for example to differentiate between quarter squats, half squats, parallel squats and full squats by observing the angle between the side-longitudinal segmental markers 14 of the torso and legs. In another example, the garments may be used to clearly monitor the change in one or more joint angles throughout a sequence of motions. For example, the garment may be used to monitor a rower's Hip-Trunk score, which is the ratio of leg angle change to trunk angle change, from catch to maximum handle. This is schematically illustrated in FIG. 10. A higher Hip-Trunk score (more than 1.5) reflects a more leg focused initial drive phase, while a lower Hip-Trunk score (less than 1.5) reflects increased trunk activity during the initial drive phase. The Hip-Trunk score describes a movement pattern which determines what produces the initial and strongest force in the stroke and can also indicate how well the rower transmits force to the boat. A coach may easily monitor an individual's Hip-Trunk score by visually tracking the side-longitudinal segmental markers 14 of the torso and legs. The coach can also simultaneously compare the side-longitudinal segmental markers 14 of the torso and legs among multiple rowers to obtain a general overview of crew movement.

In preferred embodiments, the garment further comprises at least one peripheral marker 16 visible on an exterior surface of the garment in use and positioned non-collinear with at least one of the segmental markers 2, 6, 8, 12, 14. These peripheral markers may coincide with joint centres or other anatomical landmarks such as wrists (R5, L5), elbows (R4, L4), ankles (R19, L19), knees (R15, R16, L15, L16), shoulders (R1, R2, R3, L1, L2, L3), sides of the hip (R11, L11), sides of the waist (R7, L7), calves (R18, L18). The peripheral marker 16 may be on a key segment that is also marked by a segmental marker 2, 6, 8, 12, 14. As long as the peripheral marker 16 is not aligned with the segmental marker, the peripheral marker 16 can provide useful visual indication of whole body rotation about the axis of the segmental marker.

The segmental markers 2, 6, 8, 12, 14 also provide visual indication of desirable or undesirable rotation along one of the body planes by rotation of a segmental marker relative to another, or by rotation of a peripheral marker 16 to a segmental marker. For example, when the wearer performs a squat, the wearer or a trainer can monitor rotation of the knees in the frontal plane by visually checking that the peripheral marker lines 16 along the shin remain substantially parallel to the front-longitudinal segmental markers 8 along the torso (eg to reduce knee valgus collapse).

Figure 8:
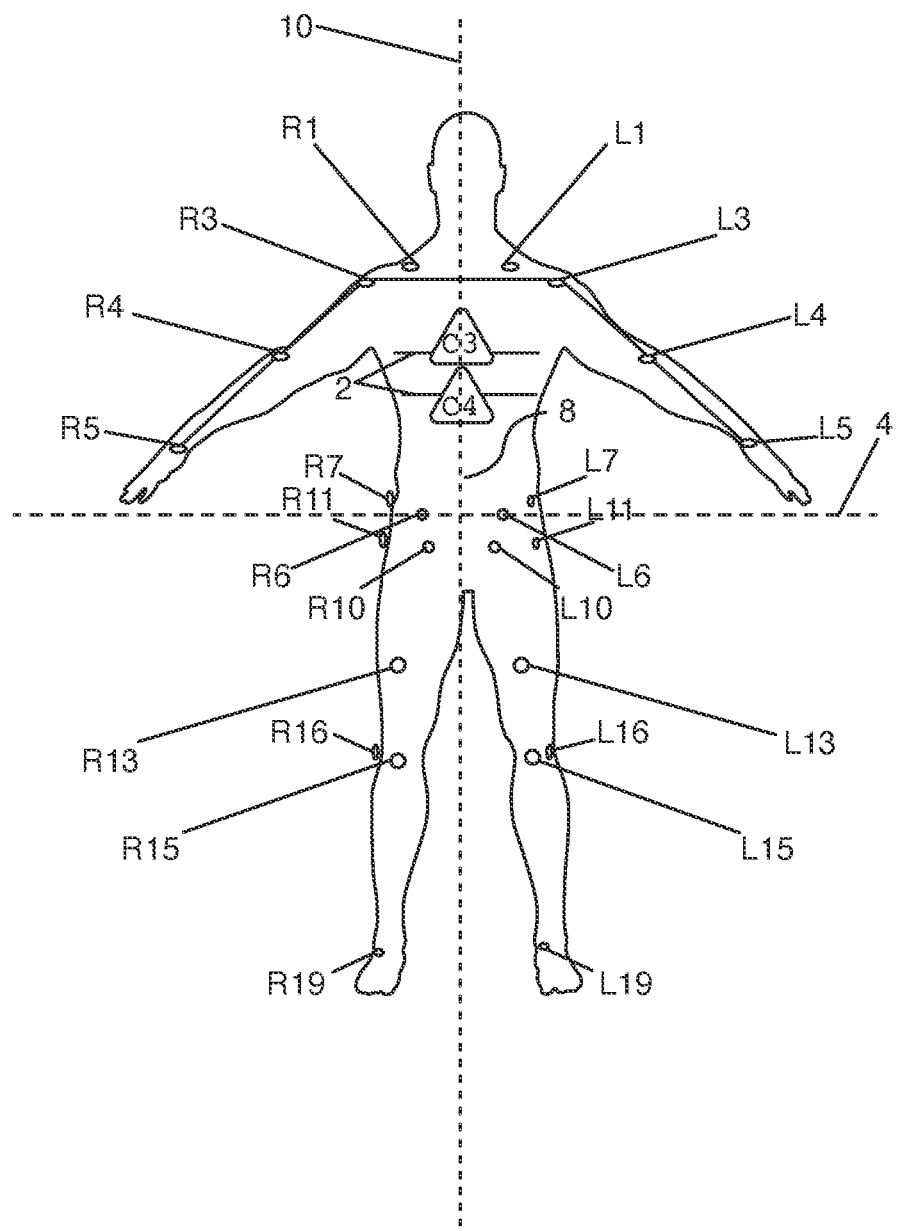
FIG. 8 is a front view of a user, illustrating positioning of segmental markers according to an embodiment of the invention.
Figure 9:
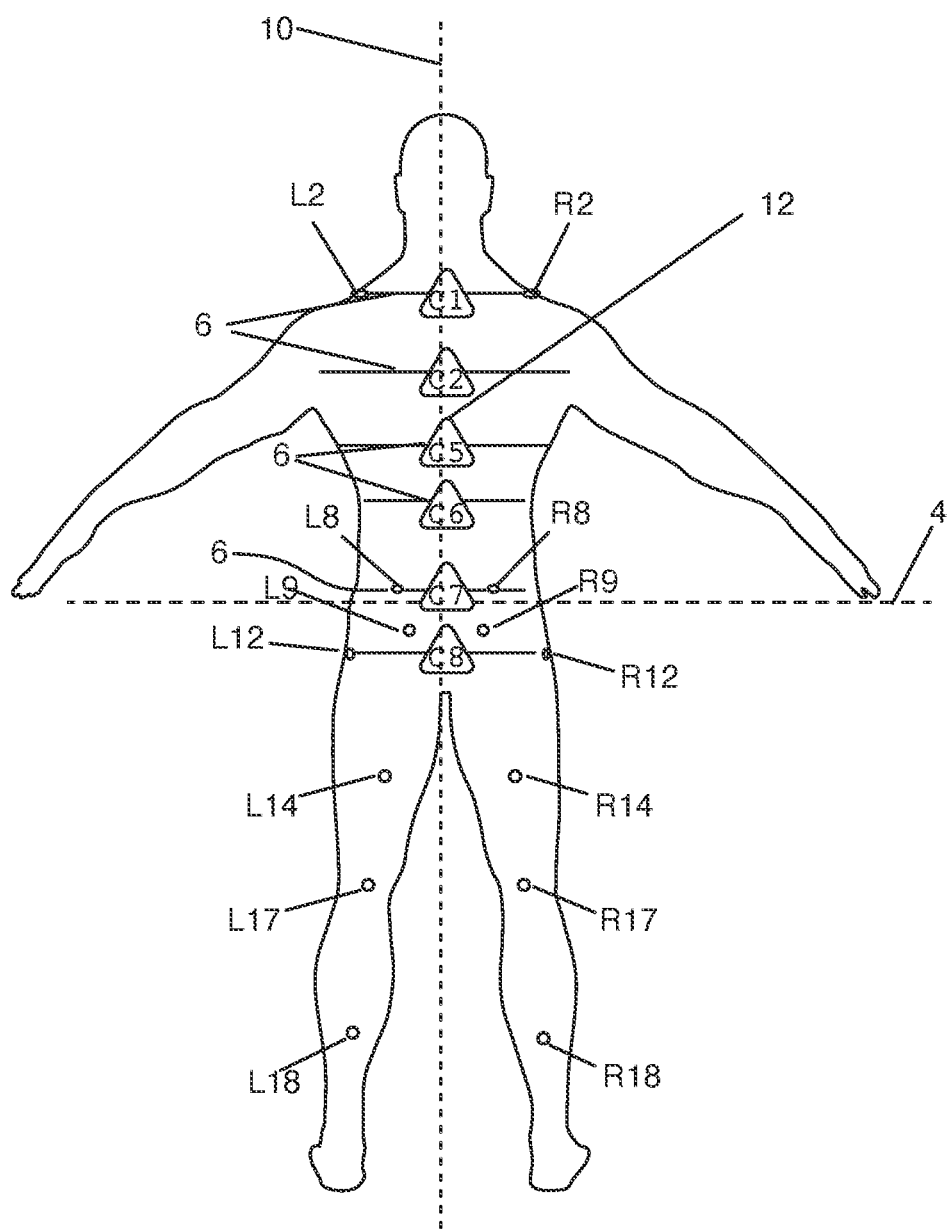
FIG. 9 is a rear view of a user, illustrating positioning of segmental markers according to an embodiment of the invention.

The segmental markers may be based on or referenced from one or more anatomical features, eg as schematically illustrated in FIGS. 8 and 9. For upper body garments eg 100, 400, 500, the front-transverse segmental marker 2 may comprise one or more marks extending across the xiphisternal axis (C3) 20, lower ribs (C4) 22, the pelvic crests (R6, L6) 24 or the anterior superior iliac crests (R10, L10) 26. The rear-transverse segmental marker 6 may comprise one or more marks extending across the upper thoracic segment (C1) 30, the middle thoracic segment (C2) 32, the lower thoracic segment (C5) 34, the lumbar segment (C6) 36, the pelvic crests (R8, L8) 38 or the posterior superior iliac crests (R9, L9) 39. The front-longitudinal segmental marker 8 may comprise one or more marks extending along the midsternal line 40, the linea alba 42, or a combination thereof. The rear-longitudinal segmental marker 12 may comprise one or more marks extending along the vertebral line 44. The side-longitudinal segmental marker 14 may comprise one or more marks extending along a side profile line such as the midaxillary line 46, the anterior axillary line, or the posterior axillary line.

For lower body garments eg 200, 600, the front-transverse segmental marker 2 may comprise one or more marks extending across the pelvic crests (R6, L6) 24 or the anterior superior iliac crests (R10, L10) 26. The rear-transverse segmental marker 6 may comprise one or more marks extending across the pelvic crests (R8, L8) 38 or across the posterior superior iliac crests (R9, L9) 39. The front-longitudinal segmental marker 8 may comprise one or more marks 52 extending between an anterior superior iliac crest (R10, L10) and the middle of the thigh (R13, L13) on one or each side of the body. The rear-longitudinal segmental marker 12 may comprise one or more marks 54 extending between the posterior superior iliac crest (R9, L9) and the middle of the thigh (R14, L14) or midpoint of the popliteal crease (R17, L17). The side-longitudinal segmental marker 14 may comprise one or more marks 56 extending between the greater trochanter (R10, L10) and the lateral femoral epicondyle (R16, L16).

For garments that cover at least part of both the upper and lower body, such as the body suit 300 illustrated in FIGS. 5 to 7, a combination or selection of the segmental markers described above may be used.

The segmental markers are selected and configured to capture key movement generators and provide visual focal points for highlighting peak flexion and extension movements, without unnecessary markers that could cause distraction, confusion or visual overload. The specific selection of segmental markers allows for multi-sport use, including rowing, cycling, paddling, swimming, athletics, weight lifting, running, walking, yoga, pilates, basketball, golf, football, tennis, baseball, gymnastics, dance, aerobics, etc.

The segmental and peripheral markers may be printed directly onto the garment material, eg using a sublimation process or an in-fabric print. Different types of markers may be coloured differently to provide stark visual contrast between for example segmental vs peripheral markers, transverse vs longitudinal markers, etc. Preferably, the remaining surface of the garment material has a substantially uniform native colour (eg black throughout) so that the markers are visually distinct from the native colour. Alternative methods of printing or otherwise marking the segmental and peripheral markers onto the garment may be used.

Embodiments of the present invention also provide a method for training for and/or coaching of various sports and physical activities. The method involves visually tracking movement of a wearer of the garment 100, 200, 300, 400, 500, 600 by observing one or more of a) displacement and/or rotation of a peripheral marker or other body portion relative to a segmental marker, b) rotation of a segmental marker relative to another segmental marker, c) displacement and/or rotation of a segmental marker relative to an external reference. The wearer may self-assess while viewing a mirror or a video recording, or a coach may assess one or more wearers (whether in real time or from a video recording).

Embodiments of the present invention also provide a system for training for and/or coaching of team sports, with multiple players in the team wearing the garment 100, 200, 300, 400, 500, 600. In addition to individual player assessment as described above, the segmental markers provide visual feedback and comparison of movement among the team members, so that the coach can assess coordination and synergies among the team members in real time and therefore offer feedback in real time. For example, body suit 300 may be applicable to the activity of rowing, and allows a coach, who would typically be ten to twenty metres or more away from a boat being rowed by the wearer, to visually observe, with greater clarity, the rowing technique being employed by the wearer. The training method afforded by the garment of the present invention also provides the coach with real time feedback on the change in the technique as the user experiences fatigue. Accordingly, the garment is able to be used by the coach not only to provide rapid feedback about incorrect technique—and hence act as a preventative measure against injuries developing—but also to inform the coach of the user tiring—and hence act as a preventative measure against overtraining. The team members may themselves compare their own movements to other teammates in real time.

Advantageously, the present training and assessment system may be used during regular training sessions instead of under artificial conditions, such in a laboratory. Further, the coach is not hampered by information overload, and does not need to learn how to interpret complicated data. Accordingly, the present invention provides a training system which assists and augments training and coaching of various sports without requiring any significant change in user behaviour. Further, in typical training environments such as a gym environment, gym users greatly outnumber coaches and/or instructors. With the use of the present garments, the instructors and/or coaches are able to more easily and quickly identify whether any given wearer is going through his or her exercises correctly. The present system allows rapid visual identification, even from a distance, of correct or incorrect movement.

Embodiments of the present invention also provide a method of training for and/or coaching of team sports using the system described above. That is, the method comprising visually tracking and comparing movement among multiple team players each wearing the garment 100, 200, 300, 400, 500, 600. This functionality becomes even more useful for team sports where users are required to act in synchronism, such as a crew of rowers for a sweep-oared boat. The visual feedback provided includes a comparison not only of the individual wearer's techniques against the reference technique required by the coach, but also a comparison of the positioning and timing of movement of the anatomical features of different team members. This allows for rapid identification of inconsistencies between the chronological movements of the wearers' respective bodies.

The present training/coaching method may further include capturing photo or video data for post analysis. It will be appreciated that the visual segmental markers on the garments allow the user to more easily identify from the photo or video all the aspects that make up current and best practice in terms of the form and function throughout the movement(s) of interest. Such functionality may be obtained using standard photo or video capturing and playback functionality, eg on a mobile device or conventional camera. Alternatively, some embodiments of the present invention provide systems comprising a computer program such as a mobile application (app) that is specially programmed to be used together with the garments to provide enhanced photo and/or video capturing and analysis.

Figure 23:
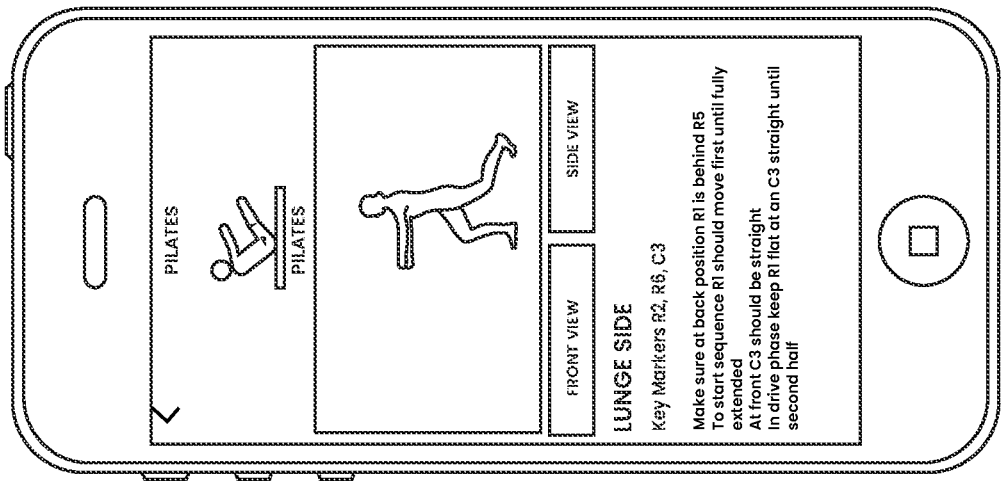
Figure 22:
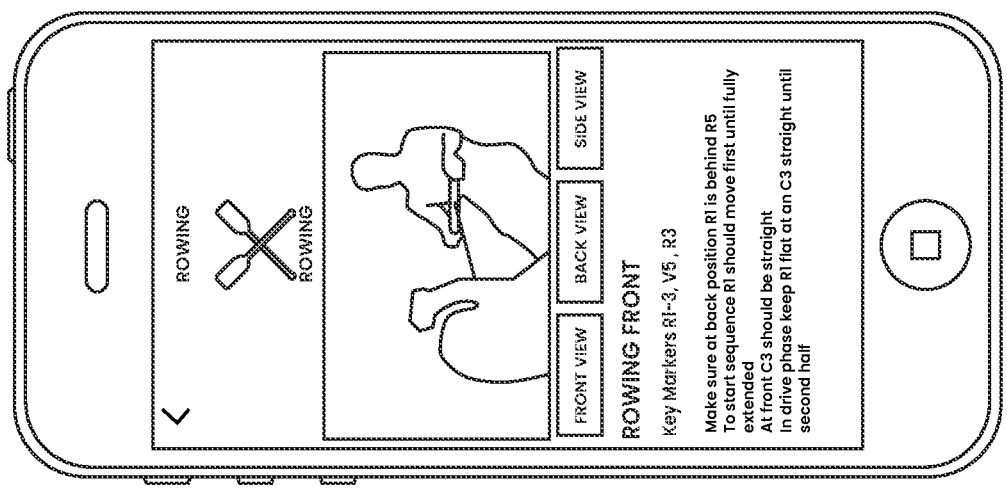
Figure 21:
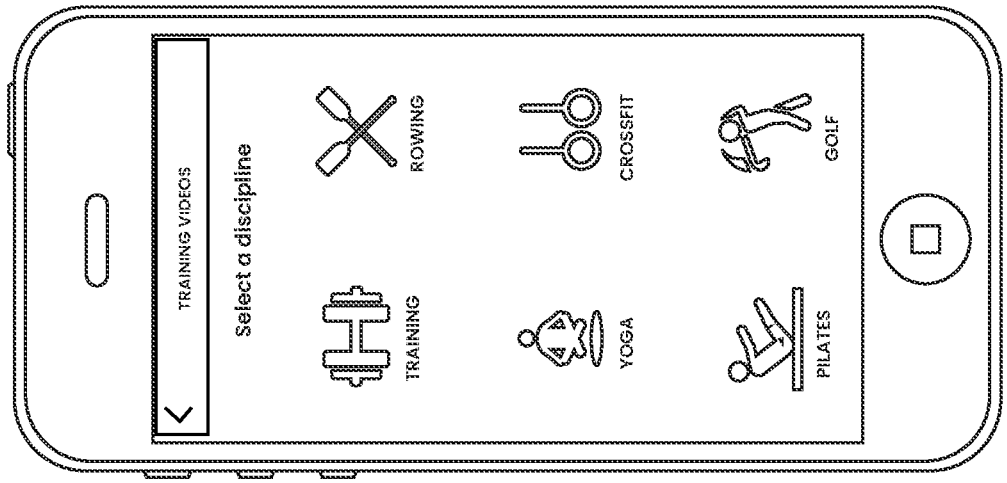

That is, the external visual markers provided by the garments 100, 200, 300, 400, 500, 600 according to the preferred embodiments are able to advantageously interact with, for example, a mobile application that runs on a smart phone with an inbuilt camera, to augment the use of the garments and provide both instructional and educational information for the user. In some embodiments, the app provides instructional information as to how to correctly reference the markers on the garments to correctly perform a movement or exercise. This information delivered by the app provides important visual cues for the user to focus on when completing the movement. This allows the individual users to better understand how to perform one or a variety of exercises and activities, and the relationship of correct form and function to the relevant segmental markers on the garments. For example, FIGS. 21 to 23 are screenshots of an example app illustrating marker-specific instructions for various physical activities. Preferably, the reference photos/videos are of demonstrators wearing the garment of the present invention. In other embodiments, markers, vectors, other geometric information or notes may be digitally superimposed upon the image of the demonstrator to replicate at least one of the markers of one or more of the garments of the preferred embodiments, for example as illustrated in FIGS. 28 to 31. In some embodiments, the app allows the user to select the nature of the garment that is to be rendered on the digitally superimposed image of the demonstrator. That is, the user may be able to select the style and colours of the superimposed markers to correspond to the garment being worn by the user. Further, the demonstrators may be industry experts, such as well-known athletes or recognised technicians, demonstrating best practice and form.

It will be appreciated that the app is software code that is executed by an electronic device, such as the smart phone referred to above, to allow that device to perform the programmed functions. In those embodiments where the electronic device is network enabled, the app is also able to selectively interact with one or more remote data sources or servers for supplementing or complimenting the functionality provided by the device. For example, in some embodiments, the electronic device, in response to the operation of the app, periodically checks a remote database to update any instructional information stored locally on the electronic device and to alert the user of the update. In other embodiments, the app allows the user to selectively upload captured image data of the user to store remotely—for example, in a cloud-based storage facility—for later reference by the user.

In other embodiments the electronic device is other than a smart phone. Examples of such other devices include singular devices having built in cameras such as a tablet device, a digital camera, a laptop computer, and the like. However, in other embodiments a digital or still camera is used in combination with the electronic device to enable the required functions.

Figure 17:
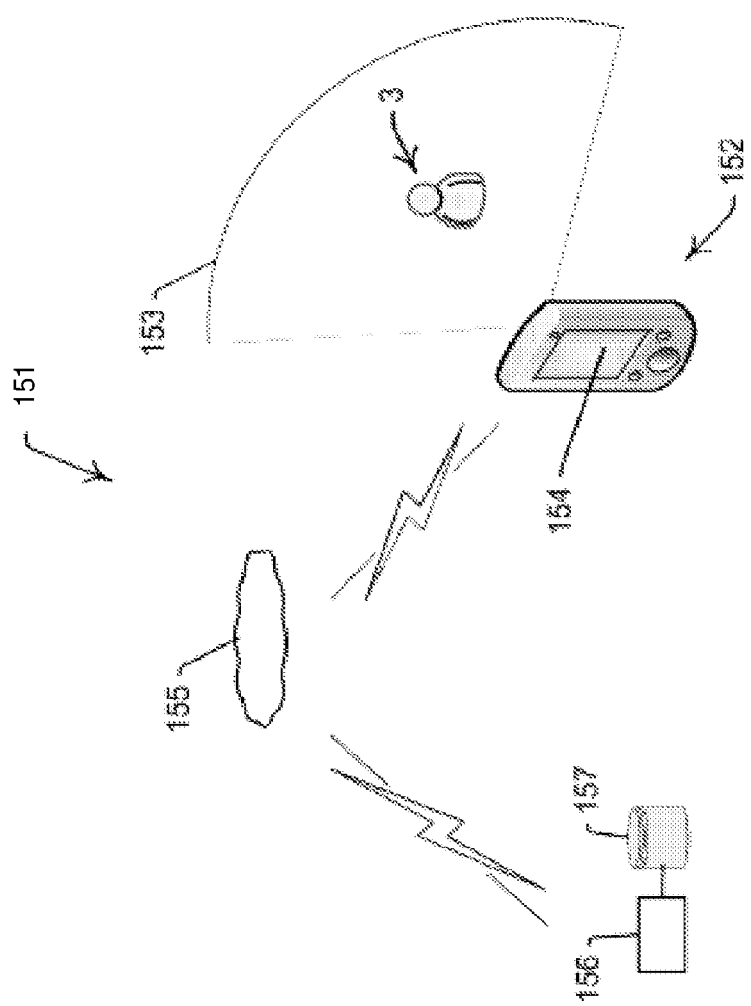
FIG. 17 is a schematic representation of an embodiment of a system for training or coaching a user wearing the garment.

An example embodiment of a system 151 for training for a physical activity is illustrated in FIG. 17. In particular, system 1 includes an electronic device in the form of a smart phone 152 having an inbuilt image capture device in the form of a digital camera. The digital camera includes a field of view 153 for capturing a time sequence of images indicative of the activity performed by user 3 in the field of view, wherein the user performs that activity while wearing a garment according to any one of the preferred embodiments described above. In one example, the smart phone 152 runs local software, in the form of an app, that is responsive to predetermined commands for storing in memory on the smart phone: a) reference instructions for a movement or sequence of movements, such as a video or photo of a demonstrator wearing a garment of the present invention, and b) a recording of the user performing the movement or sequence of movements, eg a photo or video (ie time sequence described above) of the user wearing a garment of the present invention. The app may further provide a comparison of the reference instructions and the recording of the user. The smart phone 152 also includes an integrated display 154 for displaying the comparison. Smart phone 152 is internet enabled and is able selectively, via communication network 155, to communicate with a remote server 156 to store data to and access data from, database 157. Typically, the user downloads the app to smart phone 152 and, via that app, registers with server 156. The existence of and information about accessing the app is able to be expressly included with the garments according to the invention, or separately provided.

In one embodiment, the app enables two main functions, the first of which is to allow user to access the reference instructions, in the form of training photos or videos performed by a demonstrator, which are stored within database 157, as described above.

The other main function of the app is to allow user to capture and store the recordings of the user, ie photo and/or video data of the user's body while performing the activity. That is, the user is able to view the reference instructions, and then perform the activity in field of view 153 based upon the example or other instruction in the reference instructions. It will be appreciated that smart phone 152 is able to be remotely operated either in advance by the user, or by another person, to capture recordings of the user while the user is performing the activity.

With the recordings of the user captured, the user is able to play back the recordings, eg to display the recordings on display 154, and to self-assess the movements they have recorded. This assessment is enhanced due to the user wearing a garment of the present invention. That is, the location of the relevant anatomical features will be accentuated in the recordings to facilitate the identification of any potential errors in bodily placement or timing of movement. FIGS. 19, 20, and 24-26 illustrate screenshots of an example app displaying videos recorded by the user.

Figure 26:
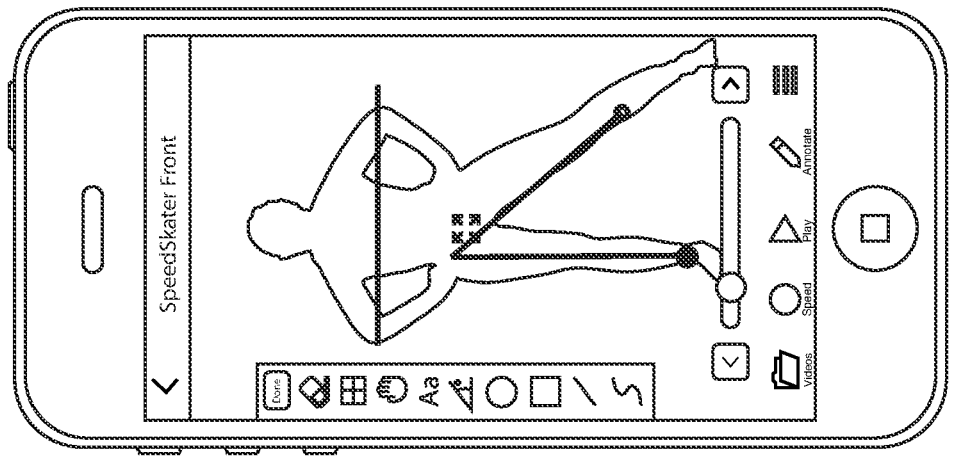
Figure 25:
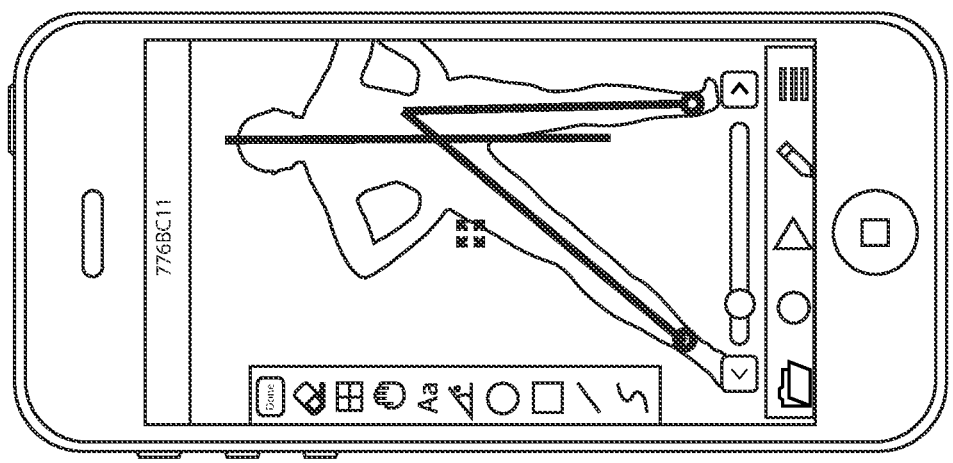
Figure 24:
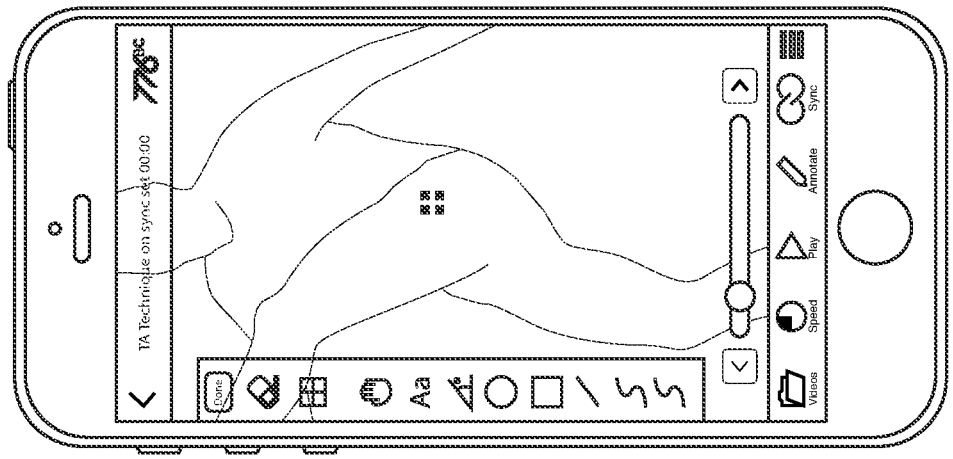
Figure 27:
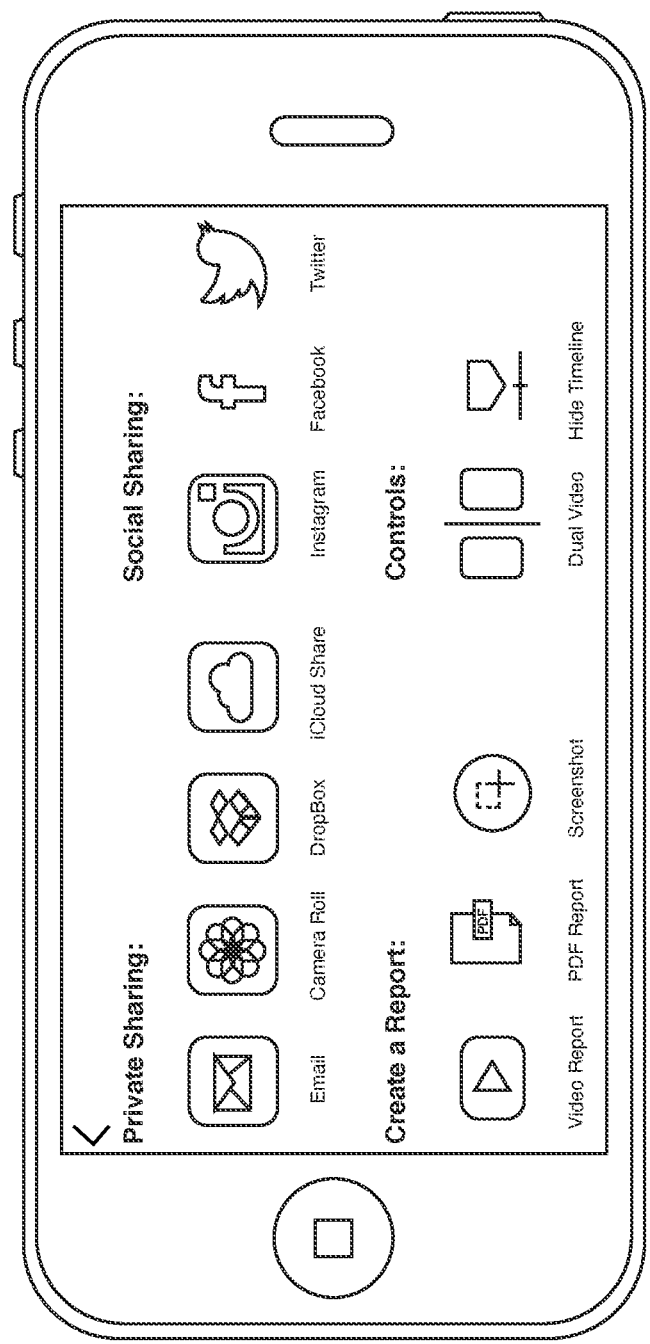
Figure 29:
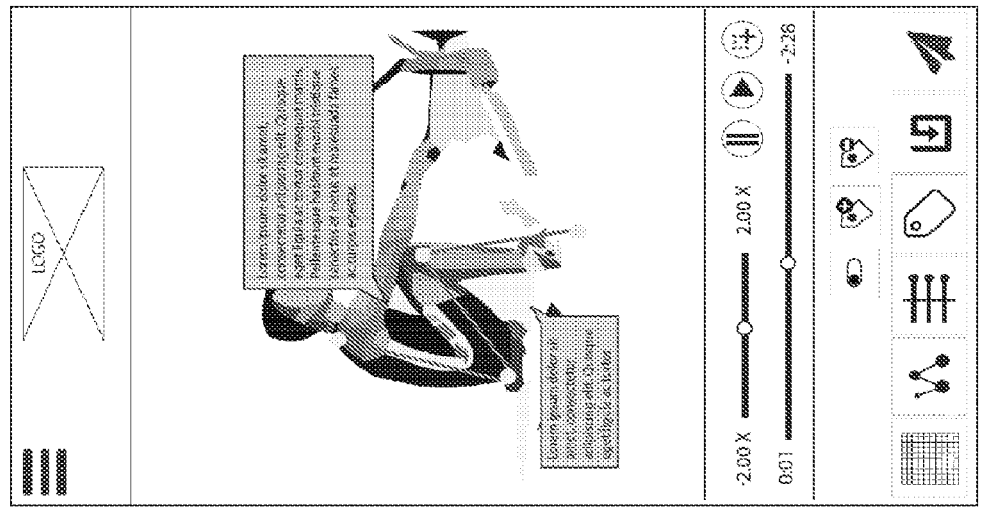
Figure 28:
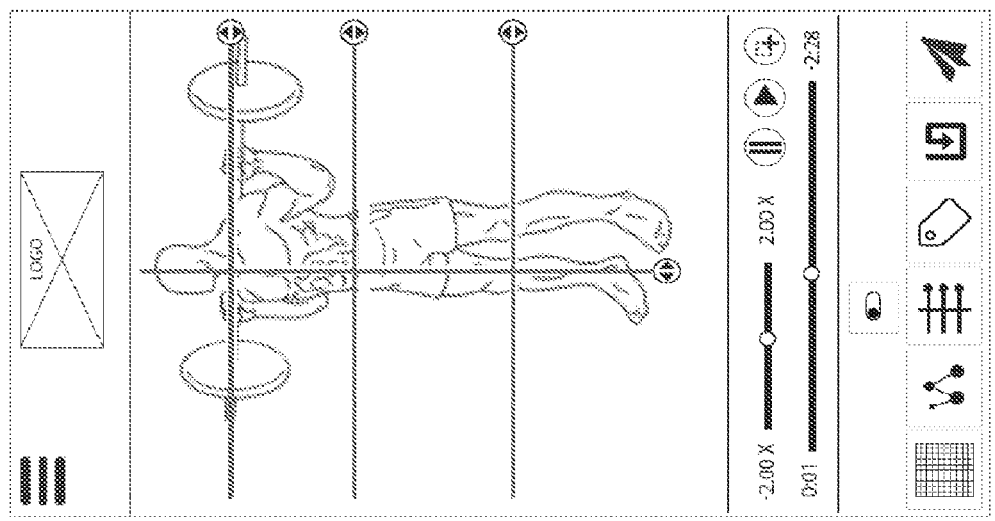
Figure 31:
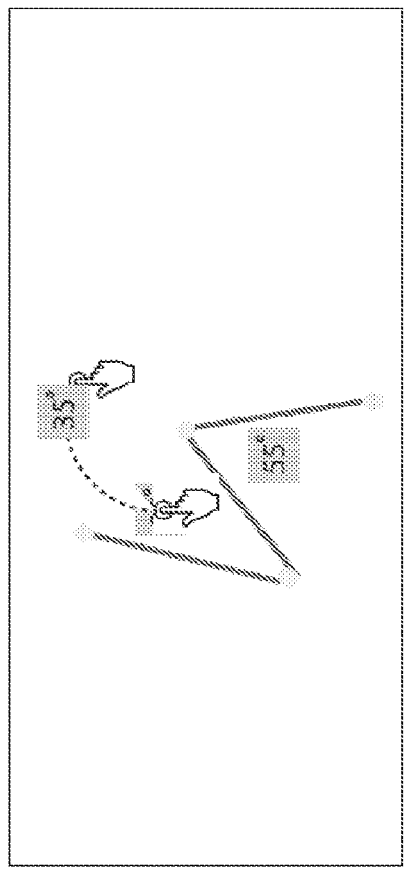
Figure 30:
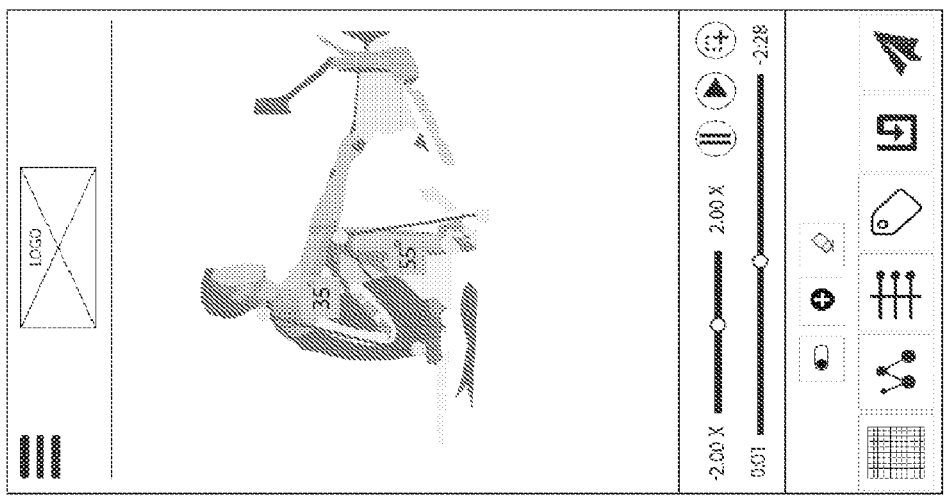

In some embodiments, the app allows the user to digitally highlight or annotate in the recordings of the user, one or more of the marker portions on the garment to enhance the ability of the user to observe inconsistencies or errors in the performance of the activity. This is illustrated in the example screenshots of FIGS. 25 and 26. The app may also automatically measure or calculate variables of interest, such as angles between recorded markers and/or digitally annotated markers, range of movement, sequence of movement, acceleration, and deceleration for display to the user, thereby providing both quantitative and qualitative information around their recorded movements. For example, the app may automatically calculate the angle of the user's legs while performing a skater exercise as shown in FIG. 26. The measurements or calculations may be displayed to the user and/or recorded to identify and quantify trends over time.

In some embodiments, the app may comprise visual recognition software to automatically identify the markers on the garment captured in a photo and/or in each frame of a video. The identification functionality may be applied in real time, for example, a video may be displayed to the user substantially simultaneously as the video is being captured, and the identification function automatically tracks relevant markers on the user's clothing to highlight these to the user and/or provide feedback in substantially real time. The automated identification functionality may additionally or alternatively be applied after the video or photo has been captured, to aid with post-analysis of the user's movements. This feature may be particularly useful to assist with analysis of multiple wearers, such as a team of rowers, to quickly and conveniently track movement of all the wearers simultaneously and with minimal user input. In some embodiments, the app may further automatically calculate, display and/or record variables of interest based on the automatically identified markers, as described above.

In one example, visual recognition may be performed using algorithmic tracking based on training sets of data. For example, the algorithm may render a line, dot or trace, and subsequently track the rendered object. This method facilitates augmented reality functionality, eg providing the user with a real time display of their movement overlaid with the rendered object. The use of depth sensing cameras may further improve the tracking capability of this example method.

In another example, visual recognition may be implemented by tracking the markers on the garments as captured on the photo or video. Specifically, the algorithm may be trained to scan a photo or key frames of a video for specific shapes or colours corresponding to the marker of interest. Once identified, the isolated marker may be tracked across all frames of the video. Useful two-dimensional positional data may be captured relative to the border of the photo or video frame, allowing for the overlay of animated lines, geometric information, etc. It will be appreciated that the visual contrast provided by the markers on the garments according to preferred embodiments of the present invention significantly facilitates the tracking algorithm. Further, the present system preferably provides only a limited number of garments marked with consistent and known colours and patterns, such that the algorithm may be easily trained on a limited selection of specific shapes or colours, to provide identification functionality that is applicable to all users of the system.

Figure 20:
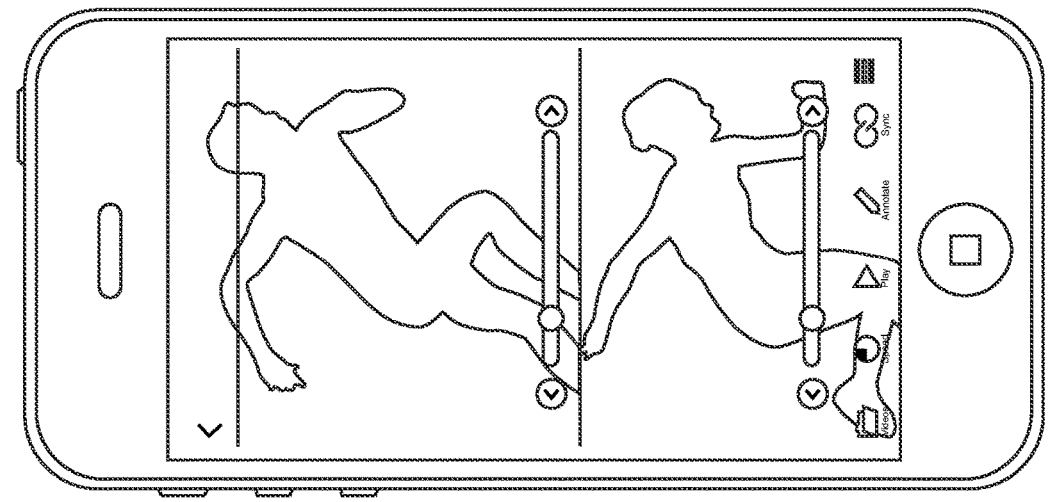
FIGS. 18 to 31 are example user interfaces generated by the system.
Figure 19:
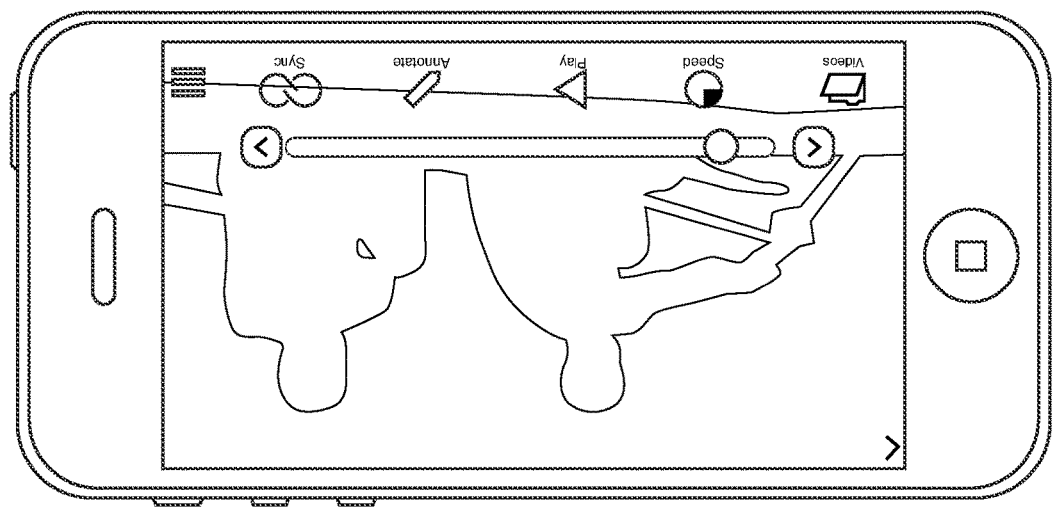
Figure 18:
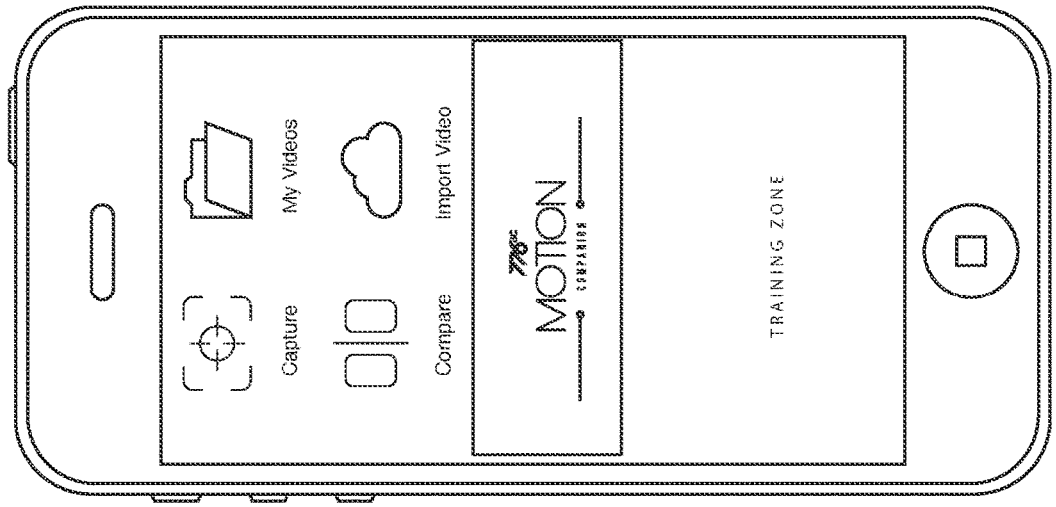

The app may also be used to compare the reference instructions and the recordings of the user. For example, corresponding photos or corresponding frames of a video may be displayed adjacent each other on the display 154, as illustrated in FIG. 20. The enables to user to visually compare their movements with the reference instructions easily and accurately. In other embodiments, the app may generate a composite video or photo comprising an overlay of the user's recording on the reference instructions. For example, the video images of the reference movement may be displayed as shadowed or ghosted form while the video images of the user's movement are overlaid in solid form. In other embodiments, the forms are reversed. The relevant markers may highlighted digitally, eg in different colours on the different images, to allow the user to more easily ascertain differences in location of the corresponding markers between the two images. In some embodiments, the comparison feature may also enable the user to compare two or more photos or videos of themselves, for example, to review their improvements in form over time.

Other exemplary functions enabled by the app may include:
   overlaying a grid on the reference instructions, the recordings of the user or the comparison display to provide additional positional information,
   adding to the reference instructions, the recordings of the user or the comparison display additional anatomical lines or points (calculated using the existing marker as a reference),
   inclusion of notes (text, voice, or otherwise) in the reference instructions, the recordings of the user or the comparison display, a variety of playback options for the reference instructions, the recordings of the user or the comparison display, including slow motion, fast motion, zoom in, zoom out, pause etc, sharing the reference instructions, the recordings of the user or the comparison display, optionally including any user-added notes, to a private or public platform.

Embodiments of the present invention provide garments, systems and methods for sports training and physical education that may be used in real time and under real training conditions, in particular when applied to skill-based sports to assist coaches and athletes with reviewing and refining technique. Embodiments of the present invention may also provide self-assessment systems and methods that are suitably affordable and uncomplicated for the amateur athlete or casual gym user, to help improve training sessions and increase safety while exercising. Embodiments of the present invention may also provide versatile training systems and methods that are useful for a variety of sports, by distilling information into key tracking data that is generic for a range of movements. Embodiments of the present invention may also provide methods and systems that are useful for training team sports, by allowing real time comparison of movement among team members to assess coordination and synergies within the team.

Embodiments of the invention have been developed primarily for sports training and have been described herein with reference to that application. However, it will be appreciated that the invention is not limited to such a field of use, and is applicable in broader contexts. For example, embodiments of the garment are also suitable for other training for private or public sector physical activities, both for individuals and groups of individuals.

For the purpose of this specification, the word "comprising" means "including but not limited to", and the word "comprises" has a corresponding meaning.

The above embodiments have been described by way of example only and modifications are possible within the scope of the claims that follow.

The invention claimed is:

1. A garment, comprising:

front and back torso portions with two shoulder portions connected to the front and back torso portions at two shoulders of a wearer, when worn;

wherein the front torso portion comprises: a vertical midline at the sagittal plane center midline of the wearer, when worn; two horizontal chest lines intersecting the vertical midline where the upper and lower ribs of the wearer, when worn; and two circles on the vertical midline where the two horizontal chest lines intersect the vertical midline;

wherein the back torso portion comprises:

a vertical spine line at the spine of the wearer, when worn;

two horizontal mid lines intersecting the vertical spine line where the mid spine and lower mid spine of the wearer, when worn;

a horizontal upper line intersecting the vertical spine line above the two horizontal mid lines where the upper spine of the wearer, when worn;

a horizontal lower line intersecting the vertical spine line below the two horizontal mid lines of the pelvic crests of the wearer, when worn; and three circles on the vertical spine line where the horizontal upper line and the two horizontal mid lines intersect the vertical spine line; and wherein the two shoulder portions comprise:

two shoulder lines at the two shoulders of the wearer, when worn; and two circles on the two shoulder lines at the two middle trapezius of the wearer, when worn.

2. The garment of claim 1, further comprising two sleeve portions extending from the two shoulder portions, wherein the two shoulder lines extend along the two sleeve portions with two circles on the two shoulder lines at the two shoulder joint centers of the wearer, when worn.

3. The garment of claim 1, wherein the two shoulder lines extend into two arm lines at the upper and lower arms of the wearer, when worn; and wherein two circles are provided on the two arm lines at the two elbows of the wearer, when worn.

4. The garment of claim 1, further comprising two side profile lines between the front and back torso portions at the two sides of the torso of the wearer, when worn; and two circles on the two side profile lines at the pelvic crests of the wearer, when worn.

* * * * *